United States Patent
Digenis et al.

(10) Patent No.: US 6,281,251 B1
(45) Date of Patent: Aug. 28, 2001

(54) IODO-NONOXYNOL-9-DERIVATIVES AND METHODS FOR THEIR USE

(75) Inventors: George Digenis; Philip Fowler, both of Lexington, KY (US); Kazuya Matsumoto, Madison, WI (US); Gustavo Doncel, Norfolk, VA (US)

(73) Assignees: University of Kentucky Research Foundation, Lexington, KY (US); The Medical College of Hampton Roads, Eastern Virginia Medical School, Norfolk, VA (US)

( * ) Notice: Subject to any disclaimer, the term of this patent is extended or adjusted under 35 U.S.C. 154(b) by 0 days.

(21) Appl. No.: 09/273,547

(22) Filed: Mar. 22, 1999

(51) Int. Cl.$^7$ ........................... A01N 31/14; C07C 43/11
(52) U.S. Cl. ................... 514/718; 514/843; 514/967; 568/608; 568/610; 424/78.24; 424/DIG. 14
(58) Field of Search .................. 568/608, 630, 568/648, 610; 424/78.24, DIG. 14; 514/843, 967, 718

(56) References Cited

U.S. PATENT DOCUMENTS

| | | | |
|---|---|---|---|
| 3,553,318 | 1/1971 | Anderson et al. | 424/184 |
| 3,954,965 | 5/1976 | Boghosian et al. | 424/81 |
| 4,795,761 | 1/1989 | Curtis-Prior et al. | 514/652 |
| 5,310,538 | 5/1994 | Bacon et al. | 424/5 |
| 5,380,523 | 1/1995 | Digenis et al. | 424/78.25 |
| 5,492,692 | 2/1996 | Digenis et al. | 424/78.25 |

OTHER PUBLICATIONS

Agha et al., "Preparation of [131I] Iodinated Nonoxynol–9," *Journal of Labelled Compounds and Radiopharmaceuticals*, vol. 21, No. 9, pp. 821–831, Apr. 1984.

Weir, et al., "Nonoxynol–9 Use, Genital Ulcers, and HIV Infection in a Cohort of Sex Workers," *Genitourinary Medicine*, 71(2):78–8 (1995).

Faundes, et al., "Spermicides and Barrier Contraception," *Current Opinion in Obstetrics and Gynecology*, 6(6):553–558 (1994).

Calamera, et al., "Determination of Membrane Integrity and Viability," Acosta, Anibal A. and Kruger, Thinus F. (eds.) *Human Spermatozoa in Assisted Reproduction*, pp. 172–192, (New York: The Parthenon Publishing Group, 1996).

Helenius, et al., "Solubilization of Membranes by Detergents," *Biochimica et Biophysica Acta*, 415, pp. 29–79 (1975).

Shachat, et al., "Mechanism of Ethylene Oxide Condensation," Schick, Martin J. (ed.), *Nonionic Surfactants*, pp. 8–42 (New York: Marcel Dekker, Inc., 1967).

Walter, et al., "High–Performance Liquid Chromatographic (HPLC) Analysis of Oligomeric Components of the Spermicide Nonoxynol–9," *Pharmaceutical Research*, 8, pp. 409–411 (1991).

Walter, et al., "Solubilization in in Vitro Spermicidal Assessment of Nonoxynol–9 and Selected Fractions Using Rabbit Spermatozoa," *Pharmaceutical Research*, 8, pp. 403–408 (1991).

Polsky, et al., "In Vitro Inactivation of HIV–1 by Contraceptive Sponge Containing Nonoxynol–9," *Lancet*, P. 1456 (1988).

Rowe, P.M., "Nonoxynol–9 Fails to Protect Against HIV–1," *Science and Medicine*, 349, p. 1074 (1997).

Cook, et al., "Do Spermicides Containing Nonoxynol–9 Prevent Sexually Transmitted Infections? A Meta–Analysis," *Sexually Transmitted Diseases*, 25(3) p. 1144–150 (1998).

Higuchi, et al., "Partical Phenomena and Coarse Dispersions," Osol, Arthur (ed.) *Remington's Pharmaceutical Sciences*, 16th Edition, pp. 294–322 (Easton, PA: Mack Publishing Co., 1980).

Sander, et al., "A Practical Method for Testing the Spermicidal Action of Chemical Contraceptives," *Human Fertility*, 6, pp. 134–137 (1941).

Resnick, et al., "Anti–HIV Screening Technology," N. Alexander, H. Gabelnick, J. Spieler (eds.), *Heterosexual Transmission of AIDS*, pp. 311–326 (New York: Wiley–Liss, 1990).

*Primary Examiner*—Rosalynd Keys
(74) *Attorney, Agent, or Firm*—McDermott, Will & Emery

(57) ABSTRACT

Mono- and di-iodinated nonoxynol-9-derivatives and methods for their use are disclosed.

18 Claims, 9 Drawing Sheets

IODO-NONOXYNOL-9-DERIVATIVES AND METHODS FOR THEIR USE

TECHNICAL FIELD

The present invention relates to mono- and di-iodinated nonoxynol-9-derivatives and methods for their use.

BACKGROUND ART

Nonionic surfactants are a preferred class of active agents for use in spermicidal formulations. For example, the nonionic surfactant nonoxynol-9 is a component in many commercially available spermicidal formulations. Spermicidal formulations are administered in the vaginal cavity for their local activity against human spermatozoa. It has been theorized that spermicidal agents exert their activity by inserting a hydrophobic moiety into the spermatozoan cell membrane. Upon insertion, the spermicidal agents disrupt the integrity of the cell membrane. This leads to an osmotic imbalance in the cell and, ultimately, cell lysis, thereby preventing sperm from fertilizing the egg and impeding conception.

Mixed experimental evidence exists as to whether nonionic surfactants used in spermicides kill human immunodeficiency virus (HIV). In vitro experiments reveal that nonoxynol-9 inactivates HIV-1 completely. The inactivation may be through a mechanism similar to that proposed for the reduction of sperm motility. The hydrophobic portion of the nonoxynol-9 molecule may associate with hydrophobic fragments on the surface of the HIV virion leading to the derangement of the viral envelope and inactivation. The hydrophobic moieties of the virion include constituent lipids, sterols and proteins of the host cell membrane from which the viral envelope stems in addition to viral proteins.

Nonoxynol-9 suffers from a number of drawbacks. For example, in vivo clinical trials of products containing nonoxynol-9 do not show clear evidence of protection against HIV infection. Certain studies indicated that HIV infection rates were essentially equal when a population of women used vaginal contraceptives containing nonoxynol-9 or a placebo. Furthermore, vaginal irritation appears to increase with increased dose of nonoxynol-9.

A need exists for compounds which are more effective at lower doses, and which can achieve equal or greater contraceptive and anti-HIV efficacy with less irritation.

DISCLOSURE OF THE INVENTION

An advantage of the present invention is the provision of compounds which are effective to prevent conception.

Another advantage of the present invention is the provision of compounds which are effective to reduce or prevent transmission of sexually transmitted diseases.

Additional advantages of the present invention will be set forth in part in the description which follows and in part will become apparent to those having ordinary skill in the art upon examination of the following or may be learned from the practice of the present invention. The advantages of the present invention may be realized and obtained as particularly pointed out in the appended claims.

According to the present invention, the foregoing and other advantages are achieved in part by a compound of the formula:

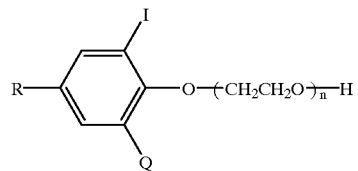

wherein R is a carbon atom containing moiety having at least 6 carbon atoms, Q is H or I, and n=1–25.

Another aspect of the present invention is a pharmaceutical composition comprising a compound of formula (I), and a pharmaceutically acceptable carrier.

A further aspect of the present invention is a method for preventing conception, the method comprising the step of administering an effective amount of a compound of formula (I).

Yet another aspect of the present invention is a method for reducing or preventing transmission of a sexually transmitted disease, the method comprising the step of administering an effective amount of a compound of formula (I).

One more aspect of the present invention relates to plastic and paper products coated with compounds of formula (I).

An additional aspect of the present invention is a process for preparing a compound of formula (I), the process comprising the steps of reacting thallium trifluoroacetate with a compound of formula:

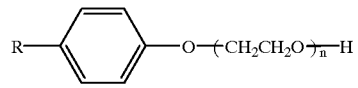

wherein R and n are as defined above to form an electrophilic thallium intermediate, and iodinating the intermediate.

Additional advantages of the present invention will become readily apparent to those skilled in this art from the following detailed description, wherein only the preferred embodiment of the present invention is shown and described, simply by way of illustration of the best mode contemplated for carrying out the present invention. As will be realized, the present invention is capable of other and different embodiments, and its several details are capable of modifications in various obvious respects, all without departing from the present invention. Accordingly, the drawings and description are to be regarded as illustrative in nature, and not as restrictive.

DESCRIPTION OF THE INVENTION

Figure 1:
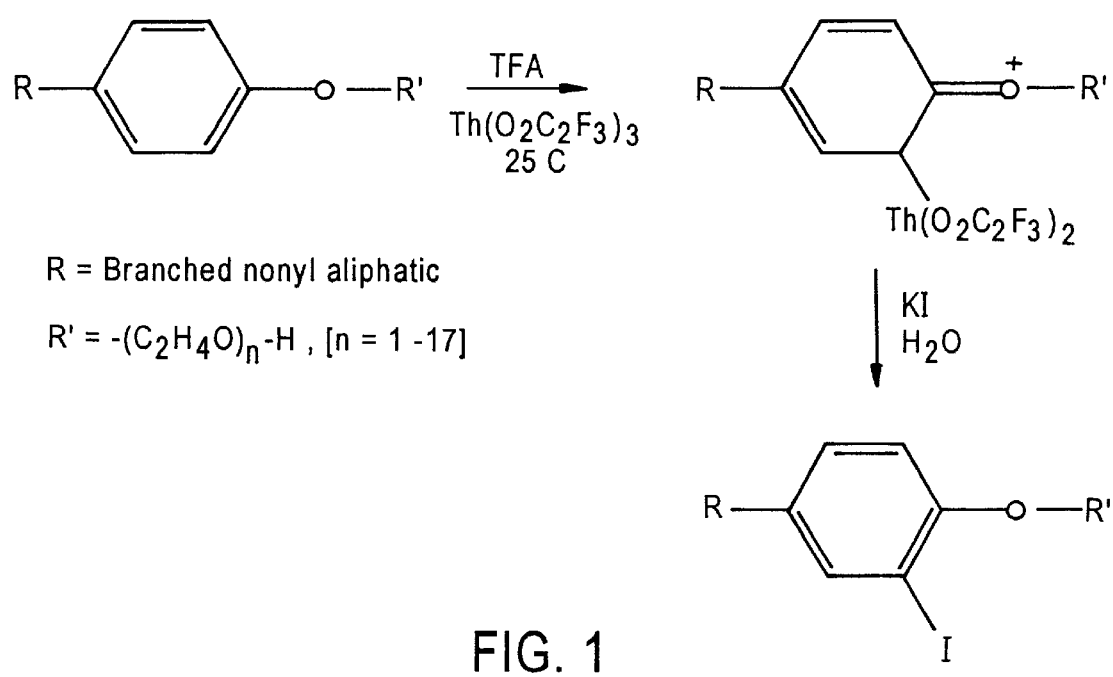
FIG. 1 illustrates an abbreviated synthetic pathway for mono-iodination of nonoxynol-9 according to the present invention.

The present invention provides compounds of the formula:

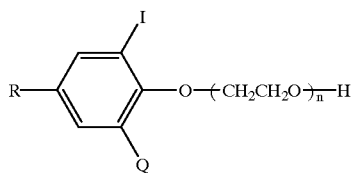

wherein R is a carbon atom containing moiety having at least 6 carbon atoms, Q is H or I and n=1–25.

The compounds of the present invention may be individual oligomers or mixtures thereof. In other words, the compounds of the present invention can be obtained from a starting material which is a multicomponent mixture of different oligomers having ethylene oxide chains with different lengths, represented by "n" which denotes the number of ethylene oxide units. The iodinated compounds can be also obtained from their respective oligomers of, for example, nonoxynol-9 by utilizing the iodination reaction described herein.

R can be any carbon atom containing moiety having at least 6 carbon atoms. Examples of carbon atom containing moieties include unsubstituted or substituted straight or branched chain alkyl groups such as octyl and nonyl; unsubstituted phenyl, biphenyl and naphthyl groups; substituted and unsubstituted aryl groups; polycyclic groups, alicyclic groups, etc.

The compounds may be mono-iodinated (Q is H) or di-iodinated (Q is I). The iodine may be, for example, 123-iodine, 125-iodine, 127-iodine and 131-iodine.

n may range from 1–25, such as, from 4 to 15 and more particularly, from 6–8. When n is 1–6, the compounds are typically water-insoluble. When n is 17–25, the compounds are typically water-soluble.

The compounds for use in the present invention can be administered as a pharmaceutical composition. The pharmaceutical compositions of the present invention comprise at least one compound of formula (I), i.e., at least one active agent, in combination with a pharmaceutical carrier or excipients.

The pharmaceutical compositions can be in any form suitable for oral administration, or for topical administration to the vagina. Suitable forms include tablets (including lozenges and granules), dragees, capsules, pills, sponges, creams, liquids, douches, gels, jellies, aerosol foams, impregnated tampons, ovules, controlled delivery device or as a lubricant on, for example, a condom or a cap diaphragm.

"Pharmaceutical composition" means physically discrete coherent portions suitable for medical administration.

"Pharmaceutical composition in dosage unit form" means physically discrete coherent units suitable for medical administration, each containing a daily dose or a multiple (up to four times) or a sub-multiple (down to a fortieth) of a daily dose of the active agent of the invention in association with a carrier and/or enclosed within an envelope. Whether the composition contains a daily dose, or for example, a half, a third or a quarter of a daily dose will depend on whether the pharmaceutical composition is to be administered once or, for example, twice, three times or four times a day, respectively.

Advantageously, the compositions are formulated as dosage units, each unit being adapted to supply a fixed dose of active ingredients. Tablets and capsules are examples of preferred dosage forms according to the invention. It is only necessary that the active ingredient constitute an effective amount, i.e., such that a suitable effective dosage will be consistent with the dosage form employed in single or multiple unit doses. The exact individual dosages, as well as daily dosages, are determined according to standard medical principles under the direction of a physician.

The active agents can also be administered as suspensions, solutions and emulsions of the active compound in aqueous or non-aqueous diluents, syrups, granulates or powders. Diluents that can be used in pharmaceutical compositions (e.g., granulates) containing the active compound adapted to be formed into tablets, dragees, capsules and pills include the following: (a) fillers and extenders, e.g., starch, sugars, mannitol and silicic acid; (b) binding agents, e.g., carboxymethyl cellulose and other cellulose derivatives, alginates, gelatine and polyvinyl pyrrolidone; (c) moisturizing agents, e.g., glycerol; (d) disintegrating agents, e.g., agar-agar, calcium carbonate and sodium bicarbonate; (e) agents for retarding dissolution, e.g., paraffin; (f) resorption accelerators, e.g., quaternary ammonium compounds; (g) surface active agents, e.g., cetyl alcohol, glycerol monostearate; (h) adsorptive carriers, e.g., kaolin and bentonite; (i) lubricants, e.g., talc, calcium and magnesium stearate and solid polyethylene glycols.

The tablets, capsules and pills comprising the active agent can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, from polymeric substances or waxes.

The active ingredient can also be made up in microencapsulated form together, with one or several of the above-mentioned diluents.

The pharmaceutical compositions which are solutions and emulsions can, for example, contain the customary diluents, such as dissolving agents and emulsifiers. Specific non-limiting examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example, ground nut oil), glycerol, tetrahydrofurfuryl alcohol, polyethylene glycols and fatty acid esters of sorbitol or mixtures thereof.

The pharmaceutical compositions will generally contain from about 0.0001 to 90 wt. %, preferably about 0.01 to 10 wt. % of the active ingredient by weight of the total composition. In addition to the active agent, the pharmaceutical compositions and medicaments can also contain other pharmaceutically active compounds.

Any diluent in the pharmaceutical compositions of the present invention may be any of those mentioned above in relation to the pharmaceutical compositions.

In addition, the present invention relates to synergistic pharmaceutical compositions wherein the active agent is complexed with polyvinylpyrrolidone (PVP). As a result of the synergy between the PVP and the compounds of formula (I), solutions with small concentrations of the inventive compounds can be used, resulting in reduced vaginal irritation.

The dosage rate, e.g., about 0.04 to about 100 mg/kg of body weight, such as about 0.01 to about 1 mg/kg will be a function of the nature and body weight of the human to be treated, the individual reaction of this subject to the treatment, type of formulation in which the active ingredient is administered, the mode in which the administration is carried out and the point in the progress of the disease or interval at which it is to be administered. Thus, it may in some case suffice to use less than a minimum dosage rate, while other cases an upper limit must be exceeded to achieve the desired results. Where larger amounts are administered, it may be advisable to divide these into several individual administrations over the course of the day.

Where it is desired to administer the compound vaginally, a vaginal suppository may be prepared by mixing the active constituents with at least one polyethylene glycol, the glycol or mixture of glycols having a melting point at or below body temperature. To facilitate the efficient dispersion of the active ingredient in the vagina, the suppository may also contain foam producing substances, such as sodium bicarbonate and sodium phosphate, and, to assure long duration of the foam, a foam stabilizing agent, such as sodium lauryl sulfate can be used.

Alternatively, a sponge may be prepared by absorbing the active constituents into a biocompatible, bioinsoluble, non-toxic sponge-like soft polymer Suitable polymers for this use are well known in the art, and include, for example, 2-hydroxyethylmethacrylate.

A cream according to this invention may contain a hydrocarbon base, such as white petrolatum, a solvent, such as glycerin or propylene glycol, and an emulsifier, such as cetyl alcohol.

Inventive formulations can be administered topically to the vaginal cavity for their local activity against human spermatozoa.

The present invention further relates to a method for preventing conception, the method comprising the step of administering an effective amount of a compound of formula (I).

By "prevention of conception" it is meant that a viable zygote cannot be formed.

In addition, the present invention relates to a method for reducing or preventing transmission of a sexually transmitted disease, the method comprising the step of administering an effective amount of a compound of formula (I). In one embodiment, the compound is administered topically to the vaginal cavity.

By "sexually transmitted disease", it is meant any communicable disease transmitted by sexual intercourse or genital contact, for example, HIV, gonorrhea and syphilis.

In the previous descriptions, numerous specific details are set forth, such as specific materials, structures, chemicals, processes, etc., in order to provide a thorough understanding of the present invention. However, the present invention can be practiced without resorting to the details specifically set forth. In other instances, well known processing structures have not been described in detail in order not to unnecessarily obscure the present invention.

EXAMPLE 1

Synthesis of Mono-iodinated Nonoxynol-9

This example describes the synthesis of mono-iodinated Nonoxynol-9.

Mono-iodinated nonoxynol-9 (IN-9) was prepared through a series of chemical reactions using nonoxynol-9 (N-9) (Igepal CO-630) (Rhone-Poulenc, lot. SP6C057657) as the starting material. Thallium trifluoroacetate (TTFA) (Aldrich Chemical Co., lot 02601KQ) (20.60 gm, 37.9 mmol) was solubilized in trifluoroacetic acid (TFA) (Fisher Biotech, lot. 955483) (50 mL, 74 gm) to yield a light brown solution. N-9 (20.23 gm, 32.84 mmol) was added to a 125 mL Erlenmeyer flask equipped with a magnetic stir bar. The TTFA-TFA solution was added dropwise over 10 minutes into the Erlenmeyer flask containing N-9 while stirring and keeping the reaction flask at room temperature and pressure. At the onset of the addition, the solution contained in the Erlenmeyer flask was light brown in color and gave way to a dark brown color over time. The solution was stirred for an additional 20 minutes to allow the thallium species to react with N-9 completely.

Potassium iodide (KI) (Aldrich Chemical Co., lot 03330PN) (40.78 gm, 245.6 mmol) was dissolved in 120 mL of deionized water and added dropwise to the flask containing the N-9 solution over a period of five minutes while stirring. During the addition of the KI solution, a dull-yellow, globular precipitate was formed in copious amounts. Thereafter, sodium metabisulfite (Aldrich Chemical Co., lot. 11824HG) (5.01 gm, 26.35 mmol) was added to the flask and allowed to stir for 10 minutes. A 10 M NaOH solution (Aldrich Chemical Co., lot. 06928T2) was added until the solution was neutralized and brought to pH=8. Near the neutralization point, the formed precipitate attained a fine, granular appearance and was bright yellow in color. At this point, the bright yellow precipitate was removed by suction filtration using a Buechner funnel, No. 1 Whatman filter paper and an Erlenmeyer filter flask.

The aqueous filtrate had a golden brown appearance and was washed with chloroform (Fisher Chemical Co., lot. 970035) (3 portions, 150 mL total) in a 250 mL separatory funnel to extract the product. The collected chloroform washings were washed with deionized water (2 portions, 100 mL total) in a clean 250 mL separatory funnel. The washed chloroform was transferred to a 200 mL Erlenmeyer flask and stirred for 4 hours with magnesium sulfate monohydrate (Aldrich Chemical Co., lot. 43418-3) to remove any residual water. A sintered glass funnel (10–15 µm pore size) was used to remove the magnesium sulfate from the solution. The chloroform layer was transferred to a 250 mL round bottom flask to remove the solvent by reduced pressure at 60° C. leaving 22.74 gm (93.1% weight recovery) of a yellow, viscous liquid. The iodine atom in IN-9 was expected to add at the ortho position of the aromatic ring relative to the polyethylene oxide side chain. The general arrangement of the synthesis of the mono-iodinated N-9 (IN-9) is shown in FIG. 1.

Figure 2:
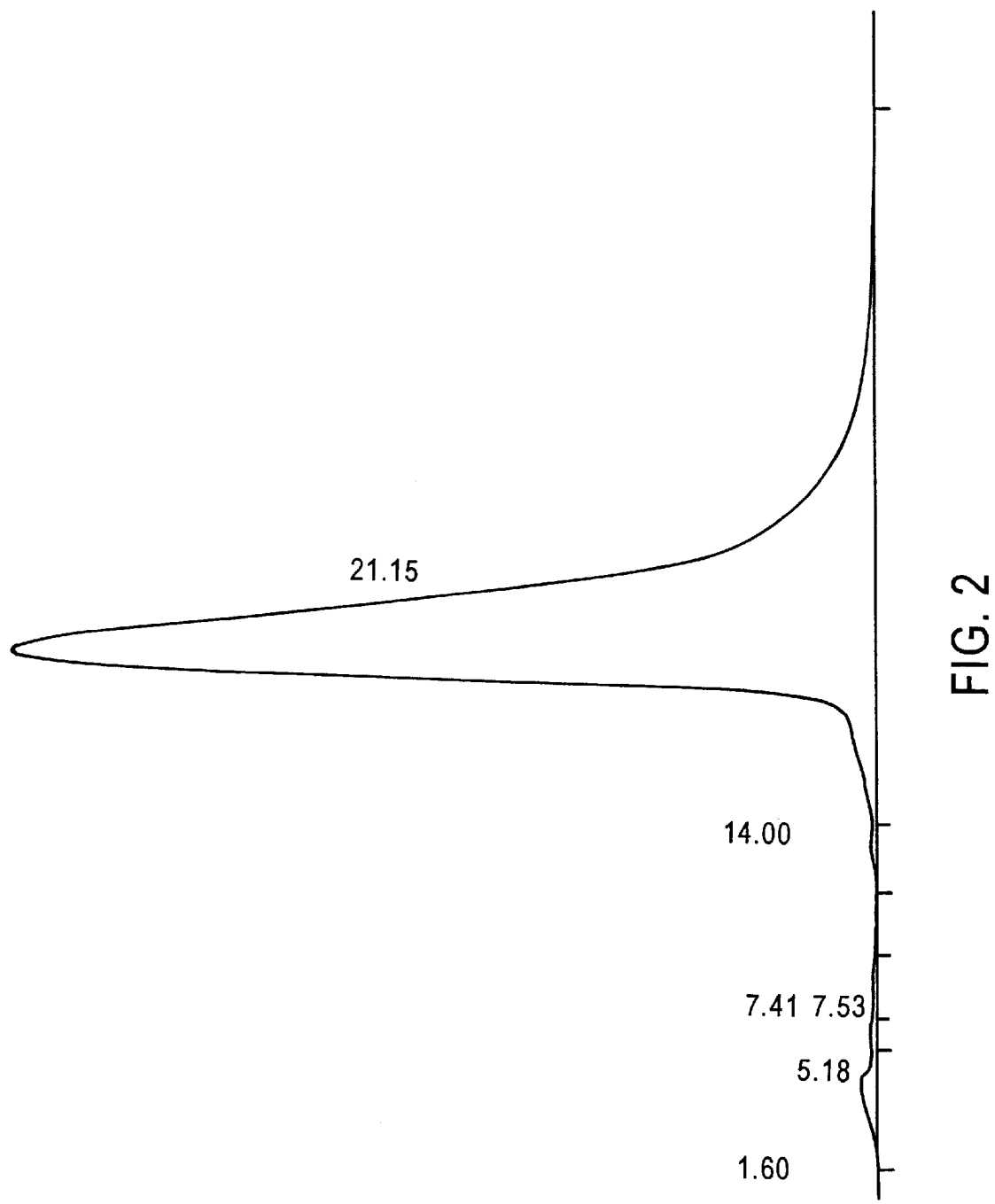
FIG. 2 illustrates a reverse-phase HPLC chromatogram of mono-iodinated nonoxynol-9 reaction product (Waters C-18 analytical column, mobile phase=methanol:water (80:20) obtained by the present invention.
Figure 3:
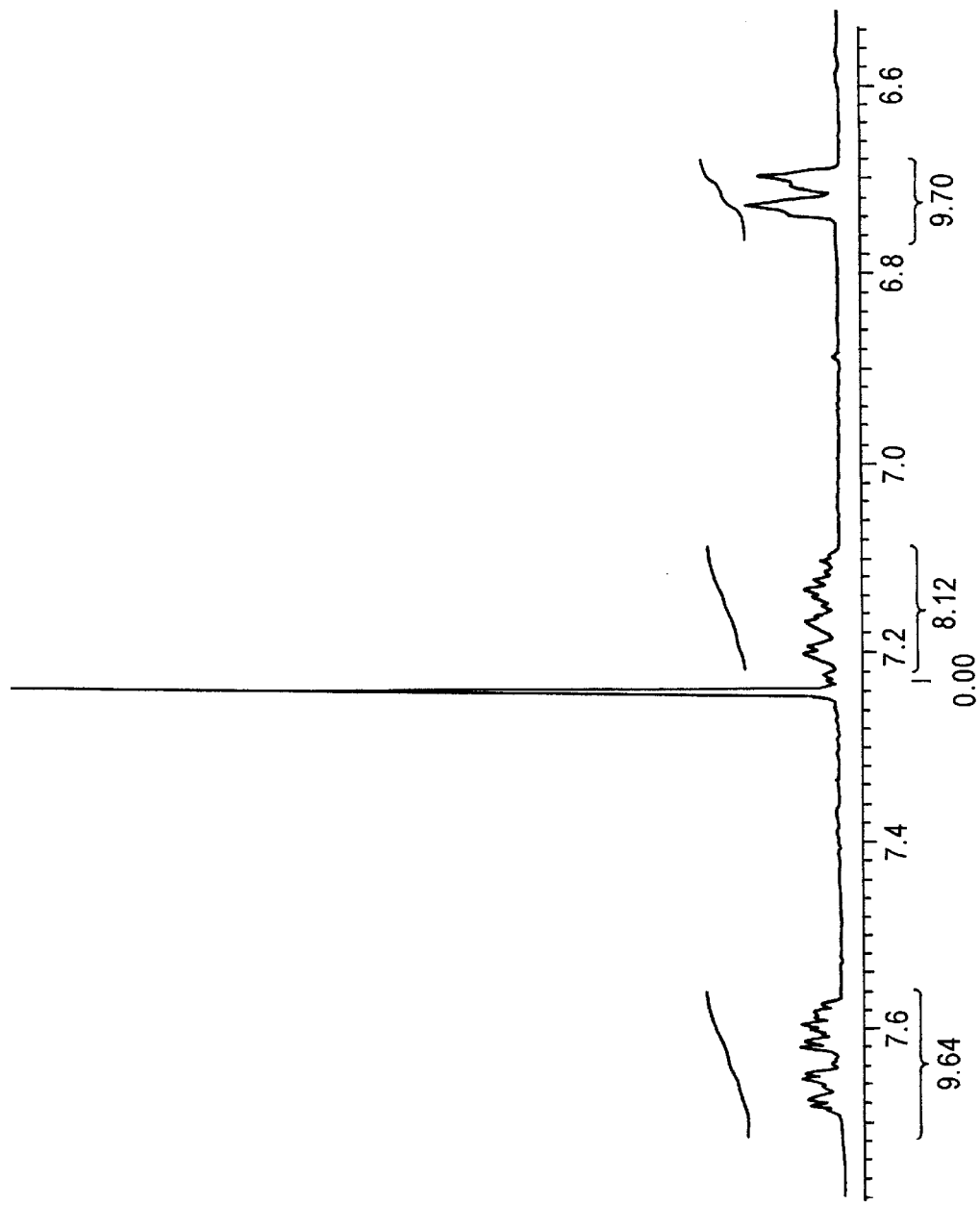
FIG. 3 illustrates the aromatic region of H-NMR of mono-iodinated nonoxynol-9 (in CDCl$_3$) according to the present invention.
Figure 4:
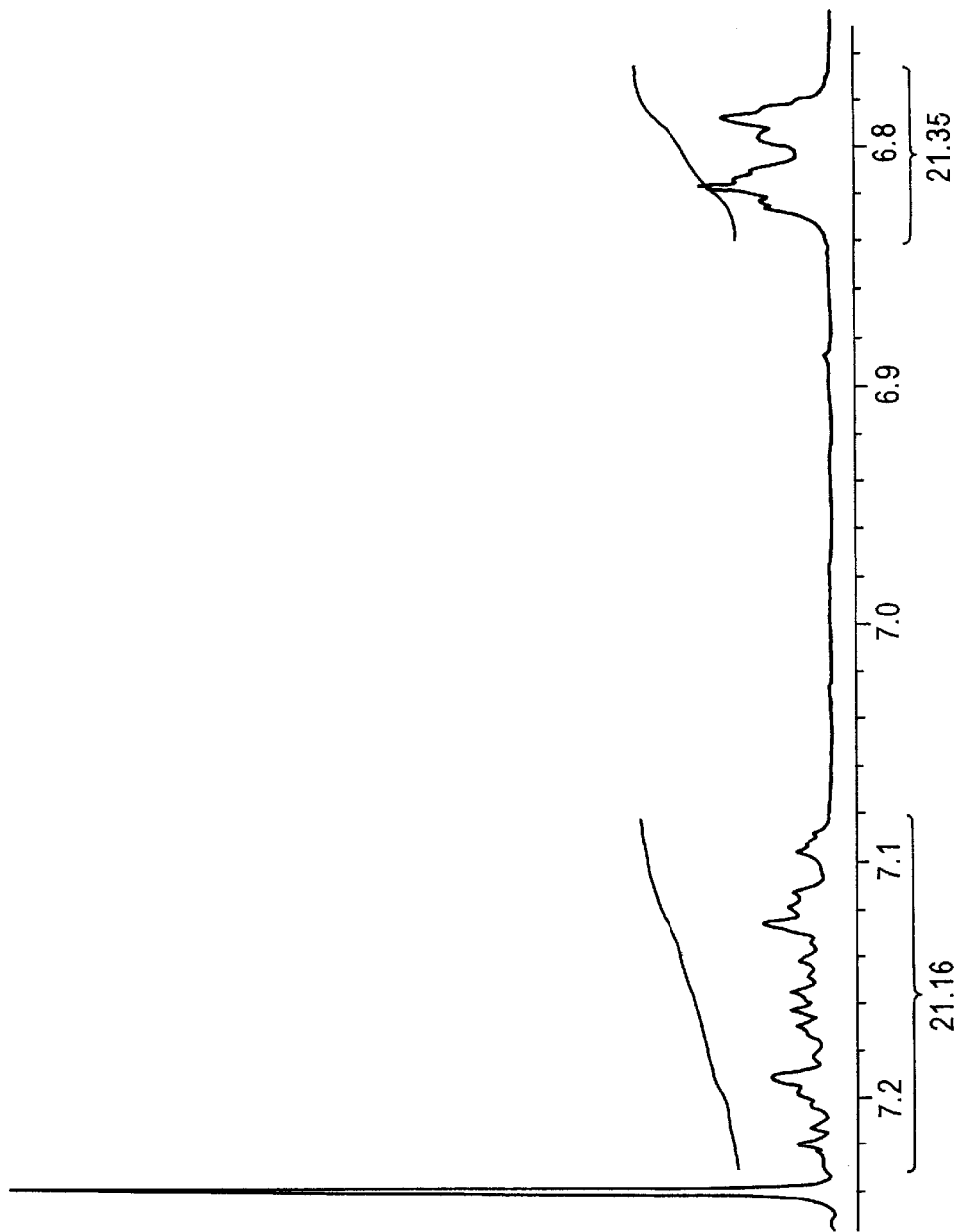
FIG. 4 illustrates the aromatic region of H-NMR of nonoxynol-9 (in CDCl$_3$).

Analysis of the resulting product indicated that virtually all of the N-9 was converted to the mono-iodinated species. The analysis of the reaction product was conducted by a reverse phase HPLC assay using a C-18 column (waters Bondapak, 3.9×300 mm, #P11061B40) with methanol/water (80:20) as a mobile phase. An ultraviolet (UV) detector set at 280 nm allowed for the detection of the product and starting material. N-9 was undetectable in the product obtained using the above HPLC procedure and only one peak, shown in FIG. 2, that of the mono-iodinated product, was observed. A H-NMR spectra, in $CDCl_3$, allowed for the quantification of protons located on the aromatic ring. As shown in FIG. 3, three peaks were detected in the aromatic region of the spectra from 6.7–7.5 ppm for IN-9 indicating three chemically distinct protons on the ring. The appearance of three distinct protons verified that an iodide atom had replaced a proton on the aromatic ring of N-9. As shown in FIG. 4, in this same region of the spectra, the spectra of N-9 revealed only two distinct protons. These spectra were consistent with the expected structural formulas of the compounds.

EXAMPLE 2

Synthesis of Di-iodinated Nonoxynol-9

This example describes the synthesis of di-iodinated Nonoxynol-9.

Figure 5:
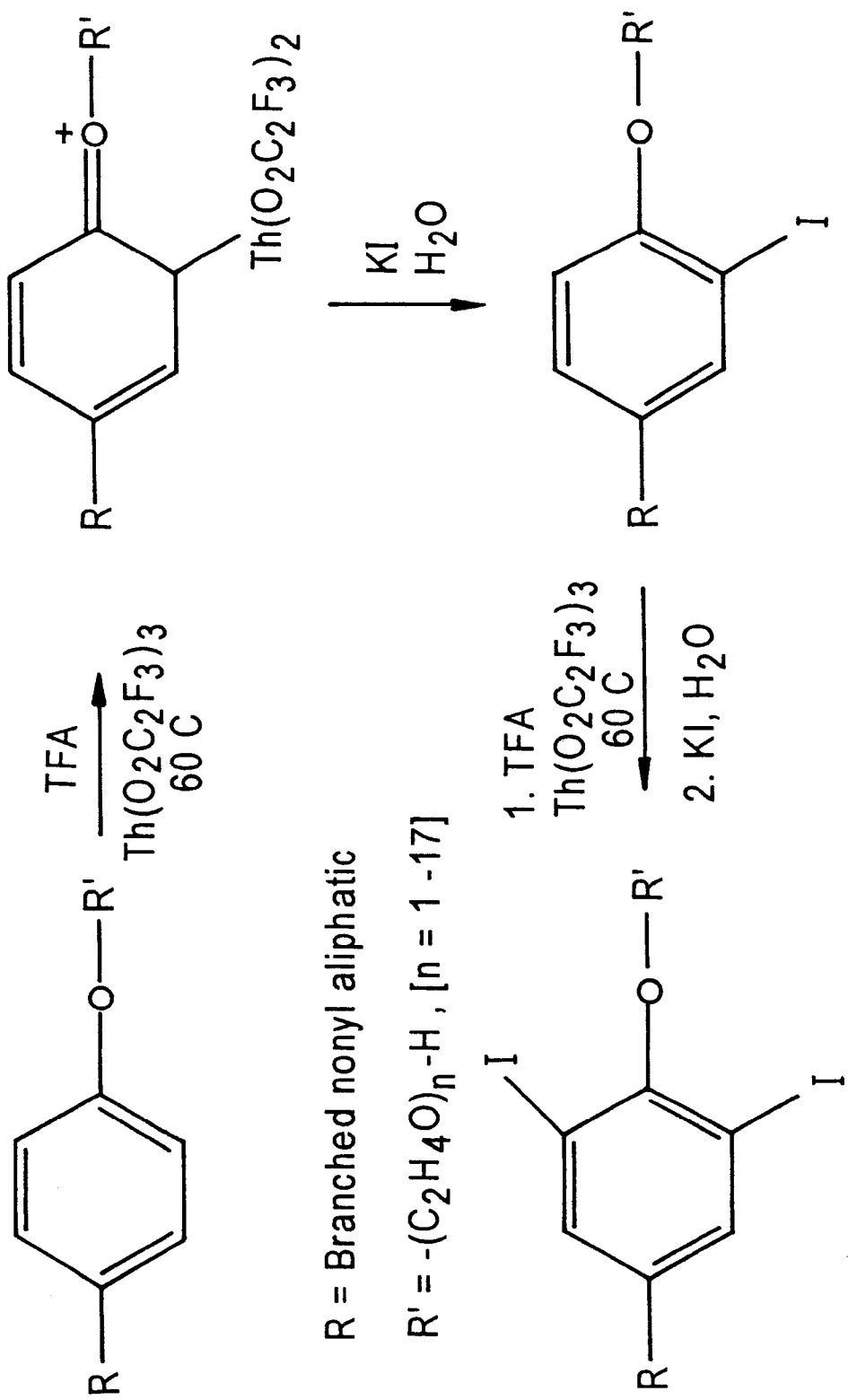
FIG. 5 illustrates an abbreviated synthetic pathway for di-iodination of nonoxynol-9 according to the present invention.

Di-iodinated Nonoxynol-9 (Di-IN-9) was prepared using chemical steps similar to those rendered to produce the mono-iodinated species. In this synthetic procedure, the following changes were incorporated. The molar ratio of TTFA to N-9 was altered to allow for the additions of two TTFA molecules per aromatic ring of N-9 (2.16 moles of TTFA to 1 mole of N-9). The dropwise addition of the TTFA/TFA solution to N-9 was conducted in a 100 mL round bottom flask with stirring. Upon the completion of the addition of the TTFA/TFA solution to N-9, the mixture was heated to 60° C. with a condenser in place for 24 hours while stirring. The amount of sodium metabisulfite was increased (10.10 gm, 53.13 mmol) in order to compensate for the increased amount of TTFA in the reaction. Otherwise, the chemical steps and the molar ratios used were precisely the same as those performed in the synthesis of the mono-iodinated species, described above. The general arrangement of the synthesis of di-iodinated N-9 (Di-IN-9) is shown in FIG. 5.

Figure 6:
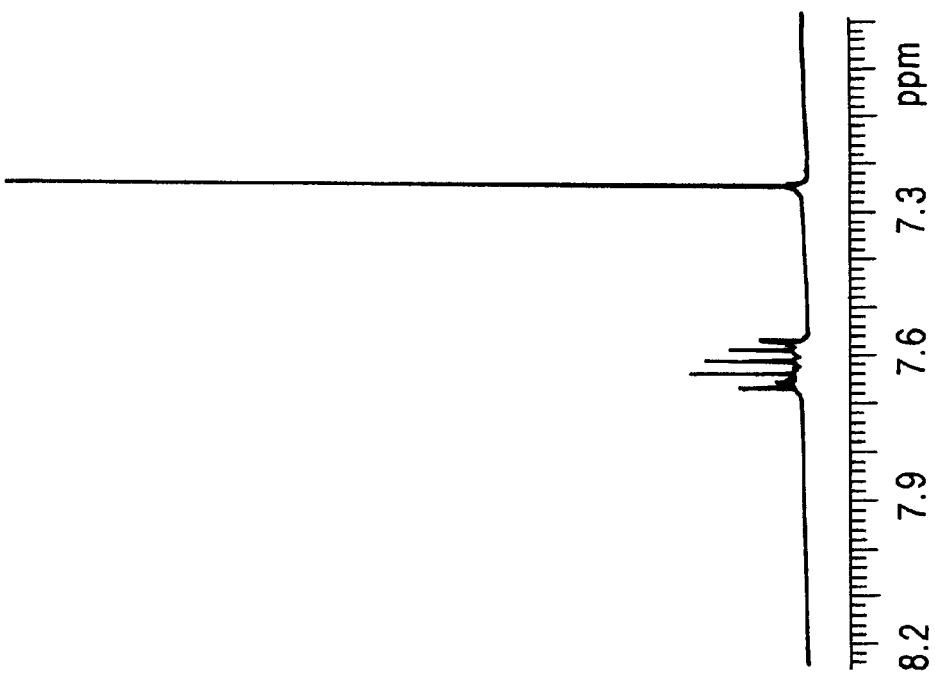
FIG. 6 illustrates the aromatic region of H-NMR of di-iodinated nonoxynol-9 (in CDCl$_3$) according to the present invention.

Analysis of the Di-IN-9 product, using the same reverse HPLC procedure mentioned previously, revealed a mixture of approximately 60% Di-IN-9 and 40% of IN-9. Both the iodide atoms in the Di-IN-9 were expected to add at the ortho positions of the aromatic ring relative to the polyethylene oxide side chain. The Di-In-9 and IN-9 species were separated by HPLC using a preparative C-18 column (Waters µ-Bondapak, 19×300 mm, # M6179101) and a mobile phase of 80% MeOH and 20% $H_2O$. As shown in FIG. 6, the H-NMR of the Di-IN-9 derivative revealed only one chemically distinct proton in the aromatic region at 7.6 ppm, which is consistent with the expected structural formula.

EXAMPLE 3

This example shows characterization data, including HLB values, retention times on the normal HPLC system and the $\log_{10}$ of their partition coefficients, for the inventive oligomers.

A simple method of comparing structurally similar surfactants can be performed by calculating the hydrophilic-lipophilic balance (HLB) of the compounds. This calculation was determined by dividing the molecular weight of the hydrophilic portion of the molecule by the molecular weight of the entire molecule. The division product was then multiplied by 100 to give a percentage, then divided by 5 to give an orderly range. For nonionic surfactants, higher HLB numbers denote more hydrophilic character. In studies determining the solubilization of various membranes by nonionic surfactants, the HLB range from 12.5–14.5 was determined to be the most effective surfactants[2]. The method of calculating the HLB numbers was employed in the comparison of N-9, IN-9, Di-IN-9 and their constituent oligomers.

A normal phase HPLC system has been devised in order to isolate the oligomers of N-9 and the iodinated derivatives of N-9 for chemical characterization. The HPLC separation of oligomers was performed on the Waters system (Millipore, Waters Chromatography, Millford, Mass.) that included two Waters Model 510 pumps, a Waters 740 Data Module, a Waters Lambda-Max Model 481 UV detector and a Waters Automated Gradient Controller. The process used the above HPLC system and a linear gradient solvent system from 98% A-2% B to 50% A-50% B over ninety minutes at a flow rate of 9.9 mL/minute (A=hexane:tetrahydrofuran, 80:20 v/v; B=2-propanol:water, 90:10 v/v). A 7-µm Zorbax-$NH_2$ preparative column (21.2×250 mm) (Rockland Technologies, Inc.) was used with the system for the separation process. A Waters solvent fraction collector was programmed so that the effluent could be collected every sixty seconds between 15 and 80 minutes after the injection of the product onto the column. The UV detector was set at 280 nm to detect the oligomers therefore allowing a trace of the effluent to be made to determine which time points would be combined. The solvent of the fractions of interest was evaporated and the oligomer identify determined by FAB mass spectrometry.

Figure 7:
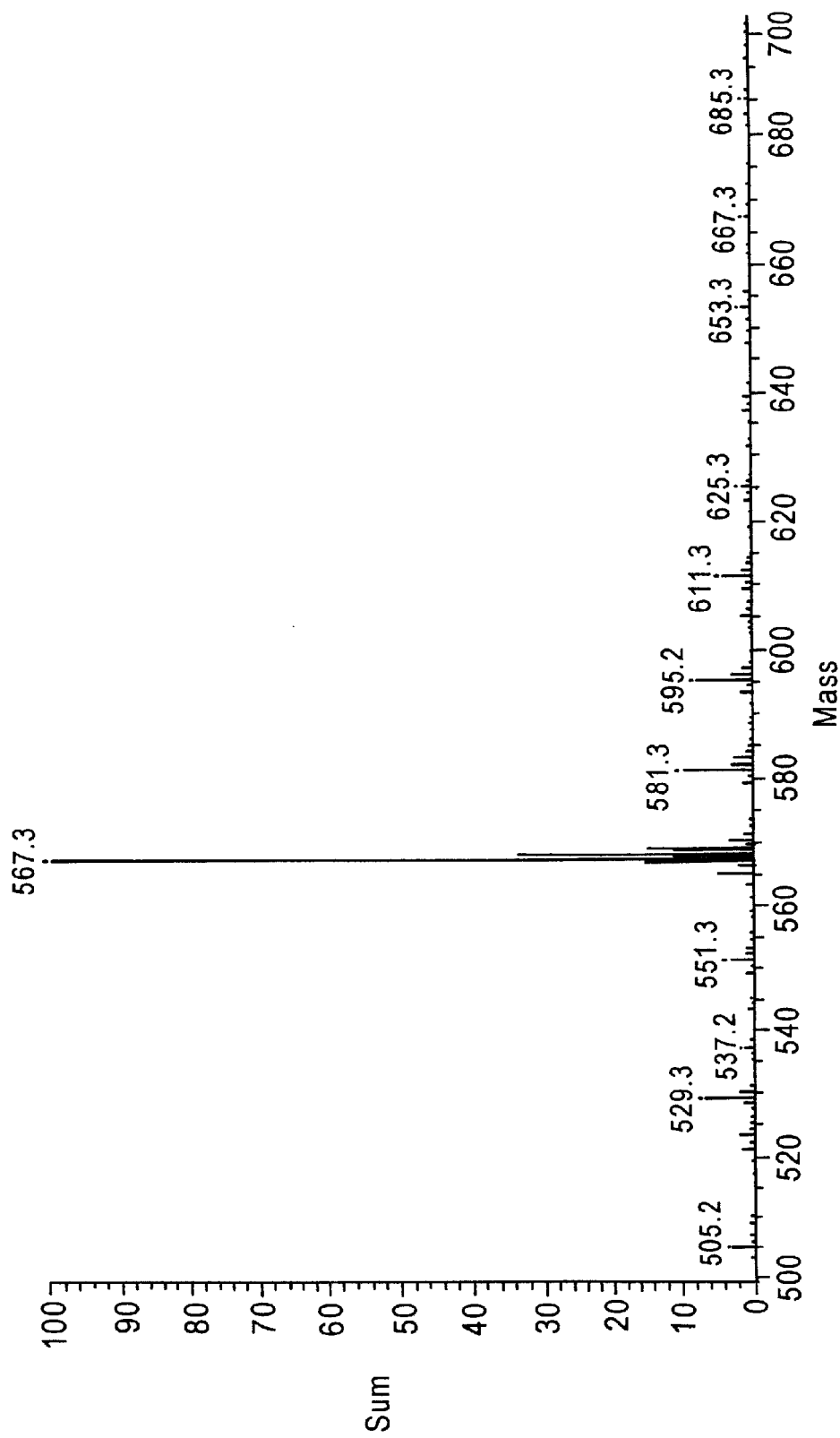
FIG. 7 illustrates a FAB mass spectral analysis for a collected nonoxynol-9 (oligomer 7, n=7) fraction.
Figure 8:
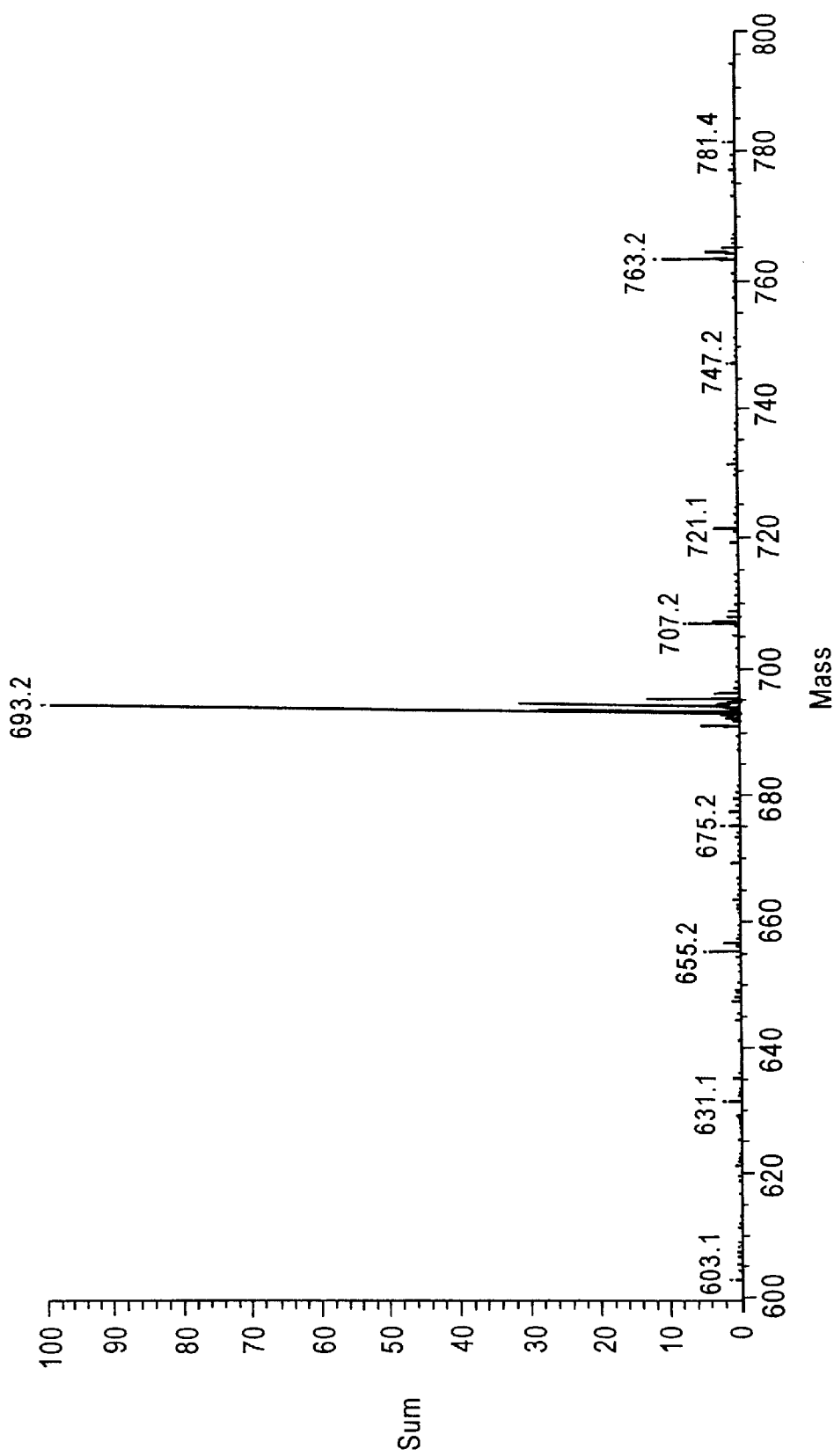
FIG. 8 illustrates a FAB mass spectral analysis for a collected mono-iodinated nonoxynol-9 (oligomer 7, n=7) fraction according to the present invention.
Figure 9:
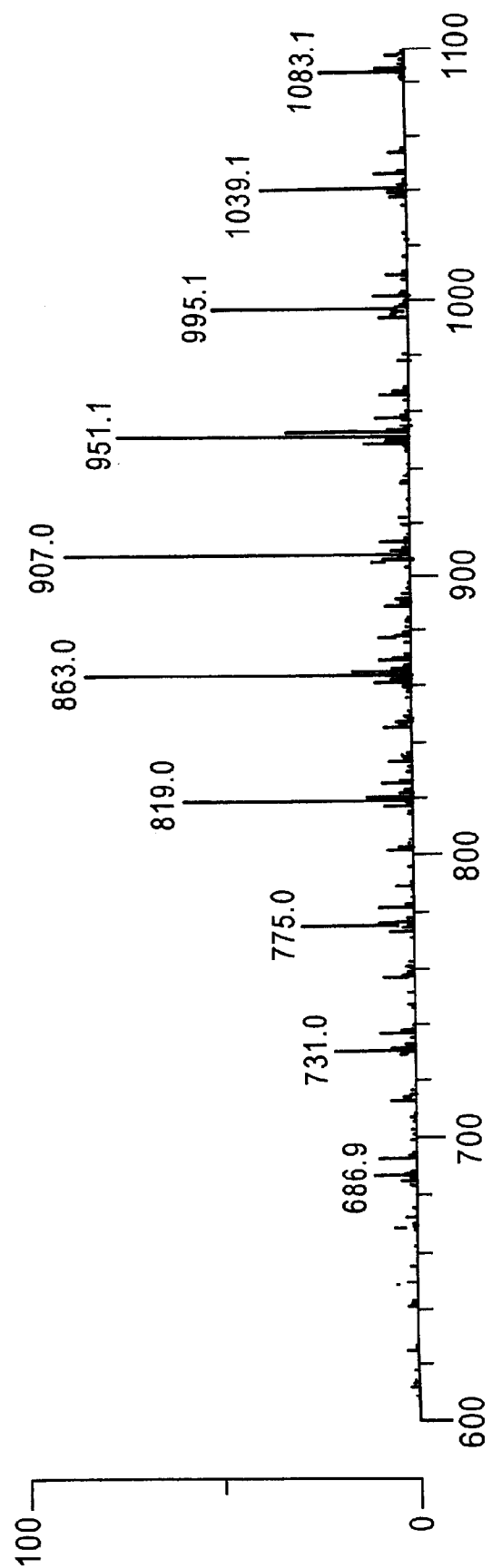
FIG. 9 illustrates a FAB mass spectral analysis for di-iodinated nonoxynol-9 (oligomers 1–17, n=1–17).

A FAB mass spectral analysis allowed for the identification of each fraction collected. The fraction believed to be the oligomer n=7 was used to determine the molecular weight for identification purposes. The calculated molecular weight of n=7 for N-9, IN-9 and Di-IN-9 were 528.7, 654.6 and 780.5 respectively. After subtraction of the mass of a potassium ratio ($K^+$), the mass spectral analysis revealed molecular weight values of 528.3, 654.2, and 779.9 for the n=7 oligomer of N-9, IN-9 and Di-IN-9 respectively (shown in FIGS. 7, 8 and 9). Once identified, the oligomers were characterized by their molecular weights, HLB values, retention times on the normal HPLC system and the $\log_{10}$ of their partition coefficients.

The experimental calculation of the log of the partition coefficient values (log P) indicated that iodinated nonoxynol-9 was more lipophilic relative to nonoxynol-9 (see Table 1). Radiolabeled species ([$^{14}$C]nonoxynol-9, [$^{125}$I]iodinated nonoxynol-9) were used to obtain precise measurements of the log P values. Iodinated nonoxynol-9 was conceptualized to be more lipophilic based upon the work by chemists such as Hammett and Hansch. Hammett determined that the halogens (F, Cl, Br, I), when attached covalently to an aromatic ring, withdrew a portion of the electron density out of the ring. The decrease in electron density causes the ring to be less susceptible to induced polarization by solvent molecules, therefore increasing its lipophilic character. The hydrophobic parameter π, developed by Hansch, reflects a substituent's ability to impart lipophilic character on a molecule ($\pi = \log P_{substituted\ molecule} - \log P_{unsubstituted\ molecule}$). Hansch found experimentally that the halogens created a positive π value in most molecular systems which correlated with an increase in the lipophilicity of the compound. With iodinated nonoxynol-9 possessing greater lipophilic character, the ethylene oxide chain can be lengthened to maintain the proper HLB. Additionally, the lengthening of the ethylene oxide chain allows for reduced irritation of the vaginal epithelial lining by reducing the formation of micelles. Nonoxynols with larger ethylene oxide chains have been shown to cause less hemolysis in erythrocytes during in vitro irritation studies. Iodide was chosen as the halogen to substitute nonoxynol-9 due to its relatively large σ and π values it produces when employed as a substituent. With an increase in the hydrophobic character, iodinated nonoxynol-9 should insert into sperm membranes more readily leading to an increase in spermicidal activity. In addition, the molecular weight and size of iodinated nonoxynol-9 is greater than that of nonoxynol-9 which leads to the possibility of the molecule being less bioavailable from vaginally placed dosage forms.

At this time, the characterization of the oligomers of Di-IN-9 has not been completed. The oligomers of interest for comparison were those with 4, 8, 11 and 13 ethylene oxide units (n=4, 8, 11, and 13). The oligomer of N-9 (n=8) was chosen since it was found to be the most abundant oligomer in the mixture[4]. IN-9 (n=13) (HLB=12.83) was selected since its calculated HLB value was most similar to that of N-9 (n=8) (HLB=12.90). The oligomers of n=4 and n=11 were chosen for the characterization of a lipophilic oligomer and an additional hydrophilic oligomer. The HLB values of the entire mixture of oligomers of N-9, IN-9 and Di-IN-9 were calculate using a weighted computation. Using this calculation, IN-9 (n=1–17) (HLB=10.56) and Di-IN-9 (n=1–17) (HLB=9.01) were theorized to be more lipophilic in character than N-9 (n=1–17) (HLB=12.80). Samples of N-9, [$^{14}$C]N-9, IN-9 and $^{125}$IN-9 were separated to compare their chemical and physical characteristics.

TABLE 1

Hydrophilic-lipophilic balance (HLB), chromatographic mobility, and partition coefficients of selected oligomers of N-9 versus the mono-iodinated nonoxynol-9 (IN-9).

Nonoxynol-9 (N-9)

| # of E.O. | Molecular Wt. | Rt[a] | HLB[b] | log P[c] |
|---|---|---|---|---|
| 4 | 398 | 23.9 ± 0.5 | 9.7 | 1.6 ± 0.05 |
| 8 | 574 | 44.2 ± 0.7 | 12.9 | 1.4 ± 0.01 |
| 11 | 706 | 60.3 ± 0.4 | 14.2 | 1.3 ± 0.07 |
| 13 | 794 | 70.0 ± 0.4 | 14.9 | ND* |

Mono-iodinated Nonoxynol-9 (IN-9)

| # of E.O. | Molecular Wt. | Rt[a] | HLB[b] | log P[d] |
|---|---|---|---|---|
| 4 | 524 | 23.5 ± 0.4 | 7.4 | 2.4 ± 0.2 |
| 8 | 701 | 43.6 ± 0.4 | 10.5 | 2.2 ± 0.1 |
| 11 | 833 | 59.4 ± 0.3 | 12.1 | 2.2 ± 0.1 |
| 13 | 921 | 68.5 ± 0.3 | 12.8 | 1.8 ± 0.1 |

*[$^{14}$C]N-9 sample (commercial) contained no N-9 (n = 13) oligomer.
[a]HPLC retention time by Zorbax-NH$_2$ preparative column (min, mean ± S.D., n = 10 for N-9, n = 12 for IN-9).
[b]hydrophilic-lipophilic balance (HLB), calculated as the molecular weight of the hydrophilic moiety (polyethylene oxide chain of N-9) divided by the molecular weight of the whole molecule times 100 and the product is further divided by five to have a scale of 0–20. (Remington's Pharmaceutical Sciences, 18th edition, p. 304, 1990)
[c]partition coefficient in n-octanol/water, as determined by [$^{14}$C]N-9
[d]partition coefficient in n-octanol/water, as determined by $^{125}$IN-9

EXAMPLE 4

Assessment of Spermicidal and Anti-HIV Properties

N-9 and its iodinated derivatives were assessed in vitro for their ability to kill spermatozoa and HIV virions. The Sander-Cramer assay was performed in order to evaluate the spermicidal activity of the surfactants and their coprecipitates with PVP. This assay determines the minimum lethal dose, reported as a concentration, of spermicide needed to kill all spermatozoa within twenty seconds. The following oligomers were incorporated into coprecipitates with PVP for the in vitro assessment: IN-9 (n=1–17), IN-9 (n=8) and IN-9 (n=13). The neat liquids of N-9 and IN-9 were also assessed for their spermicidal activity. The quantity of active compound in each coprecipitate was determined by a normal phase HPLC analysis and presented as a weight by weight (w/w) percentage. The amount of active compound in each coprecipitate was adjusted by using the w/w percentages so that the assays were conducted using equimolar amounts of active compounds. The results of the Sander-Cramer assays are shown in Table #2. The results indicate that the minimum effective concentration (MEC) needed to exhibit complete spermicidal activity for the neat liquid of IN-9 (n=1–17) (MEC–6.0 µg/mL) is over 30 times less than that needed for the neat liquid of N-9 (n=1–17) (MEC=188.0 µg/mL). The MEC values indicate that the neat compound IN-9 (n=1–17) is 30 times more effective in killing human spermatozoa than the neat compound N-9 (n=1–17) (see Table #2). The coprecipitates of IN-9 (n=8) (MEC=94 µg/mL) and IN-9 (n=13) (MEC=23 µg/mL) presented significantly different spermicidal potencies when compared to N-9 (n=1–17), suggesting that isolation of a single oligomer may be a feasible route to increase spermicidal action while decreasing irritation potential.

The compounds used in the Sander-Cramer assays (neat liquids and coprecipitates) were evaluated for their anti-HIV activity using the Cell-Free and Cell-Associated Inactivation Assays (see Table #3). Both assays employ solutions of active compound at varying concentrations in order to detect the optimal concentration to reduce the infectivity of a redetermined HIV viral load in the form of free HIV-1-RF or RF infected H9 cells. A solution of active compound is determined to have sufficient anti-viral activity if, when tested, a viral titer reduction of at least two log1, units occurs. N-9 and IN-9, in their neat liquid forms, were both found to be virucidal against cell-free and cell-associate HIV. It was determined that IN-9 (n=1–17) is at least as effective in killing HIV as N-9 (n=1–17) (see Table #3). Furthermore, IN-9 appears to be slightly more effective than N-9 against cell-associated HIV which appears to be the predominant form of HIV in male to female transmission via sexual intercourse. The coprecipitates of N-9 (n=1–17) and IN-9 (n=1–17) were also virucidal in both assays.

Acosta, Anibal A. and Kruger, Thinus F. (eds.) *Human Spermatozoa in Assisted Reproduction*, pp. 172–192. (New York: The Parthenon Publishing Group).
2. Helenius, Ari and Simons, Kai (1975). solubilization of Membranes by Detergents, *Biochimica et Biophysica Acta*, 415, pp. 29–79. (Amsterdam: Elsevier Publishing Company).
3. Shachat, Norman and Greenwald, Harold L. (1967). Mechanism of Ethylene Oxide Condensation. Schick, Martin J. (ed.) *Nonionic Surfactants*, pp. 8–42. (New York: Marcel Dekker, Inc.).
4. Walter, Brian A. and Digenis, George A. (1991). High-Performance Liquid Chromatographic (HPLC) Analysis of Oligomeric Components of the Spermicide Nonoxynol-9. *Pharmaceutical Research*, 8, pp. 409–411.
5. Walter, Brian A., Hawi, Amale A., Zavos, Panayiotis M., and Digenis, George A. (1991). Solubilization and in Vitro Spermicidal Assessment of Nonoxynol-9 and Selected Fractions Using Rabbit Spermatozoa. *Pharmaceutical Research*, 8, pp. 403–408.

TABLE 2

Spermicidal Activity Results
Sander-Cramer Assay

| Compound | Solvent | Initial Conc. ($\mu$g/mL) | N-9 Equimolar ($\mu$g/mL) | Highest Spermicidal Dilution, median | M.E.C. ($\mu$g/mL) | n | Solubility |
| --- | --- | --- | --- | --- | --- | --- | --- |
| N-9 (1–17) | dH$_2$O | 24 | 24 | 128.0 | 188.0 | 17 | OK clear soln. ph 6.5, 7.0# |
| IN-9 (1–17) | dH$_2$O | 29 | 24 | 4096.0 | 6.0 | 17 | OK hazy soln. pH 7.0, 7.5 |
| IN-9 (1–17)/PVP | dH$_2$O | 386 | 24 | 2048.0 | 12.0 | 17 | OK hazy soln. pH 5.0, 5.0 |
| IN-9 (8)/PVP | dH$_2$O | 545 | 24 | 256.0 | 94.0 | 17 | OK hazy soln. pH 5.5, 5.5 |
| IN-9 (13)/PVP | dH$_2$O | 555 | 24 | 1024.0 | 23.0 | 17 | OK cloudy soln. pH 5.0, 5.5 |
| N-9 (1–17)* | dH$_2$O | 24 | 24 | 128.0 | 188.0 | 17 | OK clear soln. pH 6.5, 6.5 |
| PVP | dH$_2$O | 100 | 0 | FAILED | N/A | 3 | OK |

*Commercial control; #Two pH determinations
N-9 = Nonoxynol-9; IN-9 = Mono-iodinated nonoxynol-9; PVP = Polyvinylpyrrolidone; M.E.C. = Minimum effective concentration; Conc. = Concentration; Soln. = Solution; n = Number of determinations

TABLE 3

Anti-HIV Activity Assessment in Cell-Free and Cell-Associated Viral Inactivation Assays

| | | Cell-Free HIV Inactivation | | | Cell-Associated HIV Inactivation | | |
| --- | --- | --- | --- | --- | --- | --- | --- |
| Compound | Solvent | Date | Conc. (%) | Infec. Red. (log)* | Date | Conc. (%) | Infec. Red. (log)* |
| N-9 (1–17) | dH$_2$O | 02/25/98 | 0.1 | >3.5 | 04/16/98 | 0.1 | 3.2 |
| | | | 0.032 | >4.5 | | 0.032 | 2.5 |
| | | | 0.01 | 2.3 | | 0.01 | 0.8 |
| | | | 0.0032 | 0.3 | | 0.0032 | 0.8 |
| IN-9 (1–17) | dH$_2$O | 02/25/98 | 0.1 | >4.5 | 04/16/98 | 0.1 | >5.0 |
| | | | 0.032 | 3.3 | | 0.032 | 2.3 |
| | | | 0.01 | 2.3 | | 0.01 | 1.8 |
| | | | 0.0032 | 0.3 | | 0.0032 | 1.0 |
| Positive Control | dH$_2$O | 02/25/98 | 0.1 | >3.5 | 04/16/98 | 0.1 | >5.0 |
| | | | 0.032 | 4.3 | | 0.032 | 1.7 |
| | | | 0.01 | 1.5 | | 0.01 | 1.0 |
| | | | 0.0032 | 0.0 | | 0.0032 | 0.7 |

*Indicates reduction of infectious viral titer of HIV-1-CF stock after a two minute incubation with the compound (reported in log units).
Only the preferred embodiment of the present invention and an example of its versatility are shown and described in the present disclosure. It is to be understood that the present invention is capable of use in various other combinations and environments and is capable of changes or modifications within the scope of the inventive concept as expressed herein.

References

1. Calamera, J. C. and Quiros, M. del Carmen (1996). Determination of Membrane Integrity and Viability.
6. Digenis, George A. and Digenis, Alexander G. (1995). High Energy Coprecipitate of Nonoxynol-9 Oligomer, PVP and Iodine Having Contraceptive and Potent Anti-HIV Properties. U.S. Pat. No. 5,380,523.

7. Digenis, George A. and Digenis, Alexander G. (1995). Coated Products with Potent Anti-HIV and antimicrobial properties. U.S. Pat. No. 5,492,692.
8. Polsky, Bruce, et al. (1988). In Vitro Inactivation of HIV-1 by Contraceptive Sponge Containing Nonoxynol-9. *Lancet*, pp. 1456.
9. Rowe, P. M. (1997). Nonoxynol-9 Fails to Protect Against HIV-1. *Lancet*, 349, 1074.
10. Cook, R. L. and Rosenberg, M. J. (1998). Do spermicides Containing Nonoxynol-9 Prevent Sexually Transmitted Infections? A Meta Analysis. *Lancet*, pg. 1456.
11. Faundes, A., Elias, C., Coggins, C. (1994). Spermicides and barrier Contraception. *Current Opinion in Obstetrics and Gynecology*, 6(6):553–558.
12. Weir, S. S., Roddy, R. E., Zekeng, L. (1995). Nonoxynol-9, use genital ulcers and HIV infection in a cohort of sex workers. *Genitourinary Medicine*, 71(2):78–8.
13. Higuchi, William I., Swarbrick, James, Ho, Norman F. H., Simonelli, Anthony P., and Martin, Alfred (1980). Particle Phenomena and Coarse Dispersions. Osol, Arthur (ed.) *Remington's Pharmaceutical Sciences*, 16th Edition, pp. 294–322. (Easton, Pa.: Mack Publishing Company).
14. Sander, F. V. and Cramer, Stanford D. (1941). A Practical Method for Testing the Spermicidal Action of Chemical Contraceptives. *Human Fertility*, 6, pp. 134–137.
15. Resnick L., Busso M. E., Duncan R. C. (1990). Anti-HIV screening technology. N. Alexander, H. Gabelnick, J. Spieler (eds.), *Heterosexual Transmission of AIDS*, pp. 311–326. (New York: Wiley-Liss).

What is claimed is:

1. A compound of the formula:

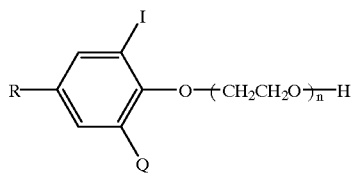

wherein R is a carbon atom containing moiety having at least 6 carbon atoms, Q is I, and n=1–25.

2. The compound according to claim 1, wherein n=8.
3. The compound according to claim 1, wherein n=9.
4. The compound according to claim 1, wherein n is from 4 to 15.
5. The compound according to claim 4, wherein n is 6–8.
6. The compound according to claim 5, wherein n=6.
7. The compound according to claim 1, wherein n=7.
8. The compound according to claim 1, which is water-soluble.
9. The compound according to claim 1, which is water insoluble.
10. The compound according to claim 1, wherein one or both iodine atoms are radioisotopes, and the iodine radioisotopes are selected from the group consisting of 123-iodine, 125-iodine and 131-iodine.
11. The compound according to claim 1, wherein R is nonyl or octyl.
12. A pharmaceutical composition comprising an effective amount of a compound of the formula:

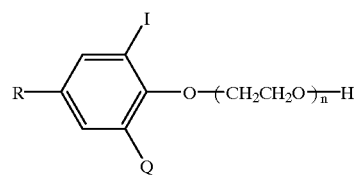

wherein R is a carbon atom containing moiety having at least 6 carbon atoms, Q is I, and n=1–25, and a pharmaceutically acceptable carrier.

13. The composition according to claim 12, in a form suitable for oral administration selected from the group consisting of tablets, lozenges, granules, dragees, capsules, and pills.
14. The composition according to claim 12, further comprising polyvinylpyrrolidone (PVP).
15. The composition according to claim 12, in a form suitable for vaginal application.
16. The composition according to claim 15, in a form selected from the group consisting of a sponge, cream, liquid, douche, gel, jelly, aerosol foam, impregnated tampon, a controlled delivery device, and a lubricant on a condom or a cap diaphragm.
17. A process for preparing a compound of claim 1 of the formula:

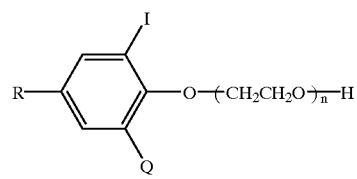

wherein R is a carbon atom containing moiety having at least 6 carbon atoms, Q is I, and n=1–25, comprising the steps of:

(a) reacting thallium trifluoroacetate with a compound of formula:

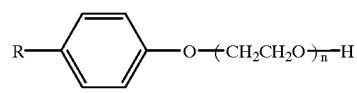

wherein Q and n are as defined above to form an electrophilic thallium intermediate, (b) iodinating the intermediate to form a monoiodinated intermediate in the ortho-position;

(c) then further reacting with additional thallium trifluoracetate to form a monoiodinated electrophilic thallium intermediate; and (d) reacting the intermediate with additional iodonatino reactant to form a compound of claim 1.

18. The process of claim 17, further comprising:
   isolating at least one iodinated oligomer.

* * * * *